United States Patent
Staedler et al.

(10) Patent No.: US 12,012,587 B2
(45) Date of Patent: Jun. 18, 2024

(54) BACTERIAL OIL TREATMENT COMPOSITION FOR HANDLING A DECOMMISSIONED OIL CABLE

(71) Applicant: TIBIO SAGL, Comano (CH)

(72) Inventors: Davide Staedler, Comano (CH);
Thibaud Spinetti, Lausanne (CH);
Marco Torriani, Breganzona (CH)

(73) Assignee: TIBIO SAGL, Comano (CH)

( * ) Notice: Subject to any disclaimer, the term of this patent is extended or adjusted under 35 U.S.C. 154(b) by 0 days.

(21) Appl. No.: 17/639,161

(22) PCT Filed: Jul. 29, 2020

(86) PCT No.: PCT/EP2020/071347
§ 371 (c)(1),
(2) Date: Feb. 28, 2022

(87) PCT Pub. No.: WO2021/037465
PCT Pub. Date: Mar. 4, 2021

(65) Prior Publication Data
US 2022/0315884 A1    Oct. 6, 2022

(30) Foreign Application Priority Data
Aug. 27, 2019 (EP) .................................. 19193792

(51) Int. Cl.
| | |
|---|---|
| *C12N 1/20* | (2006.01) |
| *A62D 3/02* | (2007.01) |
| *C12N 1/16* | (2006.01) |
| *C12P 1/04* | (2006.01) |
| *C12R 1/10* | (2006.01) |
| *C12R 1/125* | (2006.01) |
| *C12R 1/39* | (2006.01) |

(52) U.S. Cl.
CPC ............... *C12N 1/20* (2013.01); *A62D 3/02* (2013.01); *C12N 1/165* (2021.05); *C12P 1/04* (2013.01); *C12R 2001/10* (2021.05); *C12R 2001/125* (2021.05); *C12R 2001/39* (2021.05)

(58) Field of Classification Search
CPC .......... C12N 1/20; C12N 1/165; C12N 1/205; A62D 3/02; C12P 1/04; C12R 2001/10; C12R 2001/125; C12R 2001/39; C12R 2001/01
See application file for complete search history.

(56) References Cited

FOREIGN PATENT DOCUMENTS

| | | |
|---|---|---|
| DE | 20 2019 104 226 U1 | 8/2019 |
| KR | 10-2015-0062130 A | 6/2015 |
| WO | 2015/191582 A1 | 12/2015 |
| WO | 2018/055587 A1 | 3/2018 |

OTHER PUBLICATIONS

J.D. Van Hamme et al., Microbiology and Molecular Biology Reviews, Dec. 2003, vol. 76, No. 4, p. 503-549. (Year: 2003).*
Kim et al., J Korean Soc Appl Biol Chem (2014), vol. 57, 5-14. (Year: 2014).*
Rapp et al.; "Formation of exopolysaccharides by and partial characterization of a heteropolysaccharide of high molecular weight;" Applied Microbiology and Biotechnology; 1979; p. 67-78; vol. 7, No. 1.
Molnár et al.; "Enhanced biodegradation of transformer oil in soils with cyclodextrin—from the laboratory to the field;" Biodegradation; 2005; pp. 159-168; vol. 16, No. 2.
Towell et al.; "The biodegradation of cable oil components: Impact of oil concentration, nutrient addition and pioaugmentation;" Envrionmental Pollution; 2011; pp. 3777-3783; vol. 159, No. 12.
Zhao et al.; "Selection of functional consortium for crude oil-contaminated soil remediation;" International Biodeterioration & Biodegradation; 2011; pp. 1244-1248; vol. 65, No. 8.
Oct. 14, 2020 Search Report issued in International Patent Application No. PCT/EP2020/071347.
Oct. 14, 2020 Written Opinion of the International Searcing Authority issued in International Patent Application No. PCT/EP2020/071347.
Nov. 25, 2021 International Preliminary Report on Patentabiity issued in International Patent Application No. PCT/EP2020/071347.

* cited by examiner

*Primary Examiner* — Kade Ariani
(74) *Attorney, Agent, or Firm* — Oliff PLC

(57) ABSTRACT

An improved bacterial oil treatment composition or pool for handling a decommissioned oil cable, which may be laid in particular as part of a power grid in the ground. The invention further relates to a bacteria growth culture medium containing the bacterial oil treatment composition for refurbishing an oil cable and a corresponding use.

7 Claims, 5 Drawing Sheets

FIG: 3
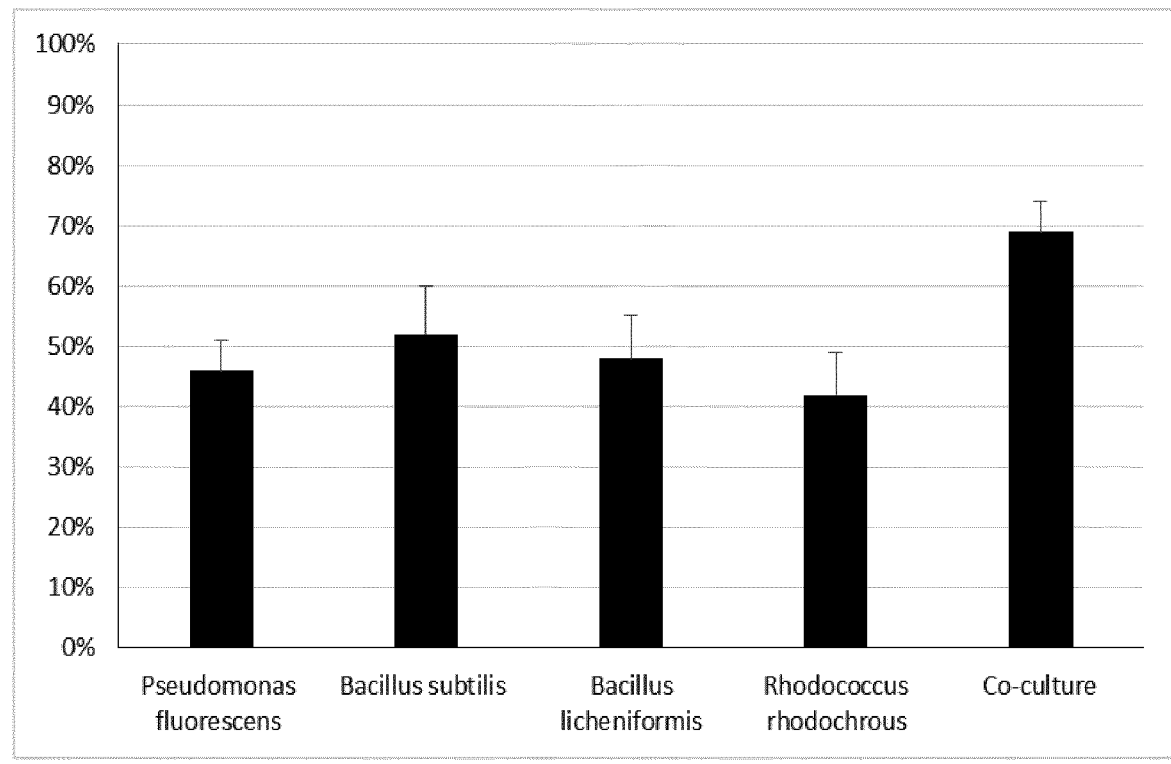
FIG: 4
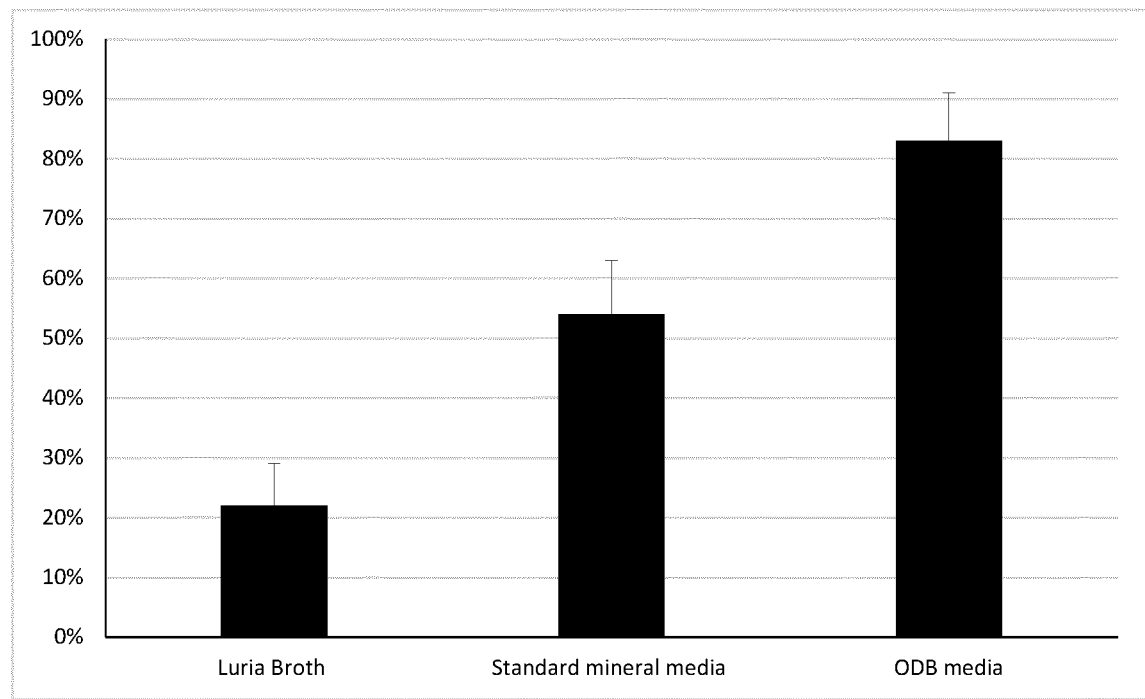

FIG: 5
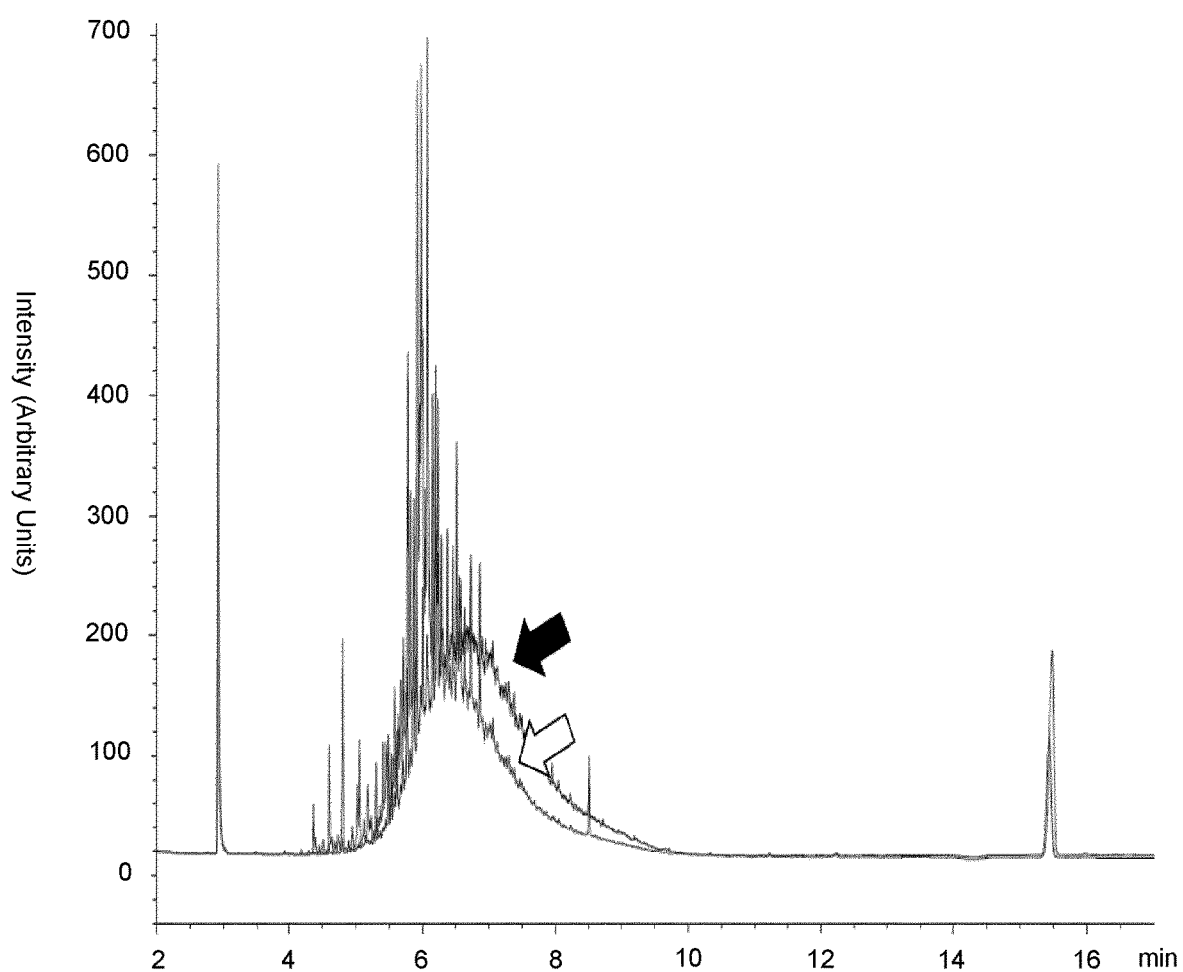

FIG: 6
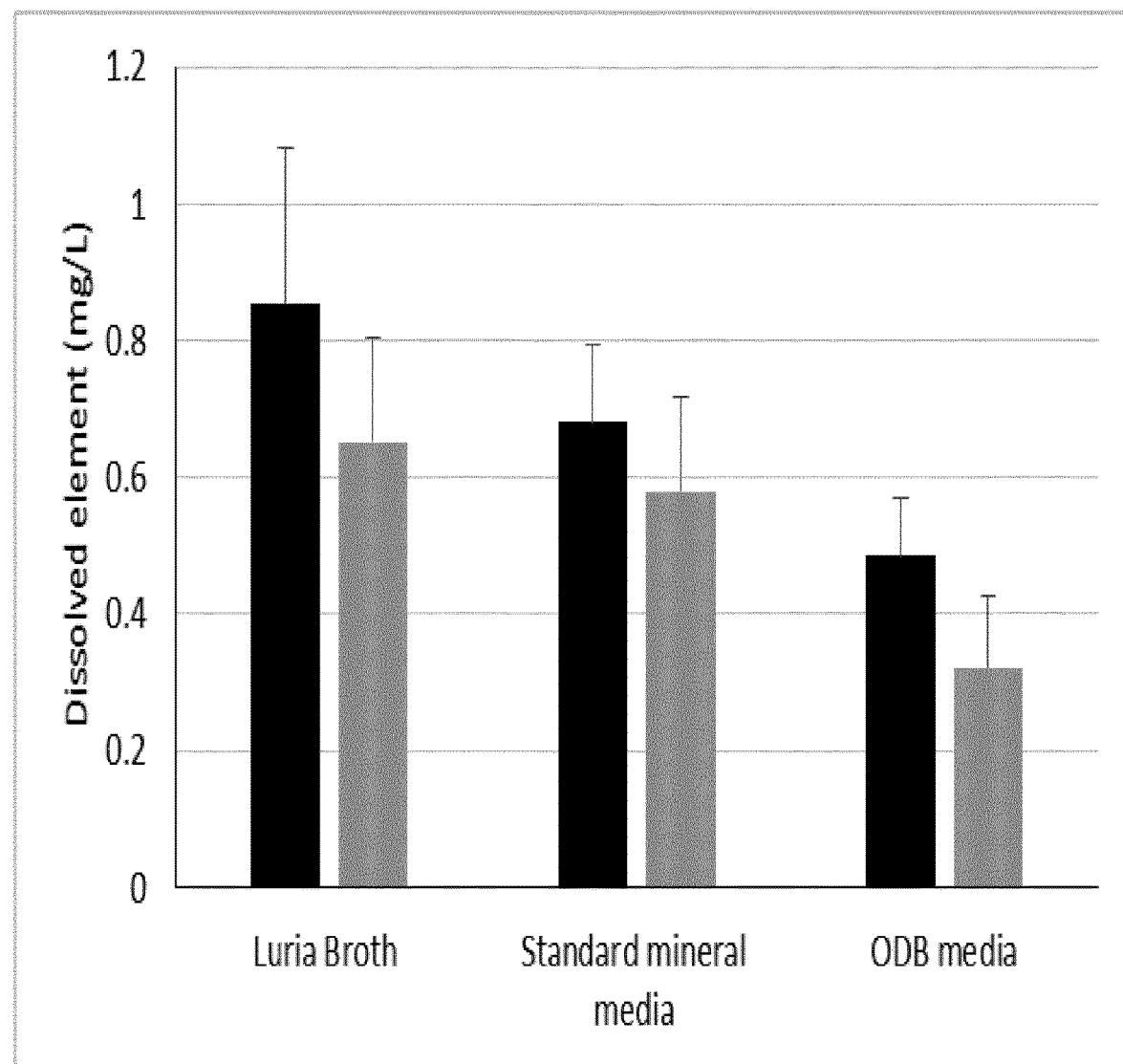

FIG: 7
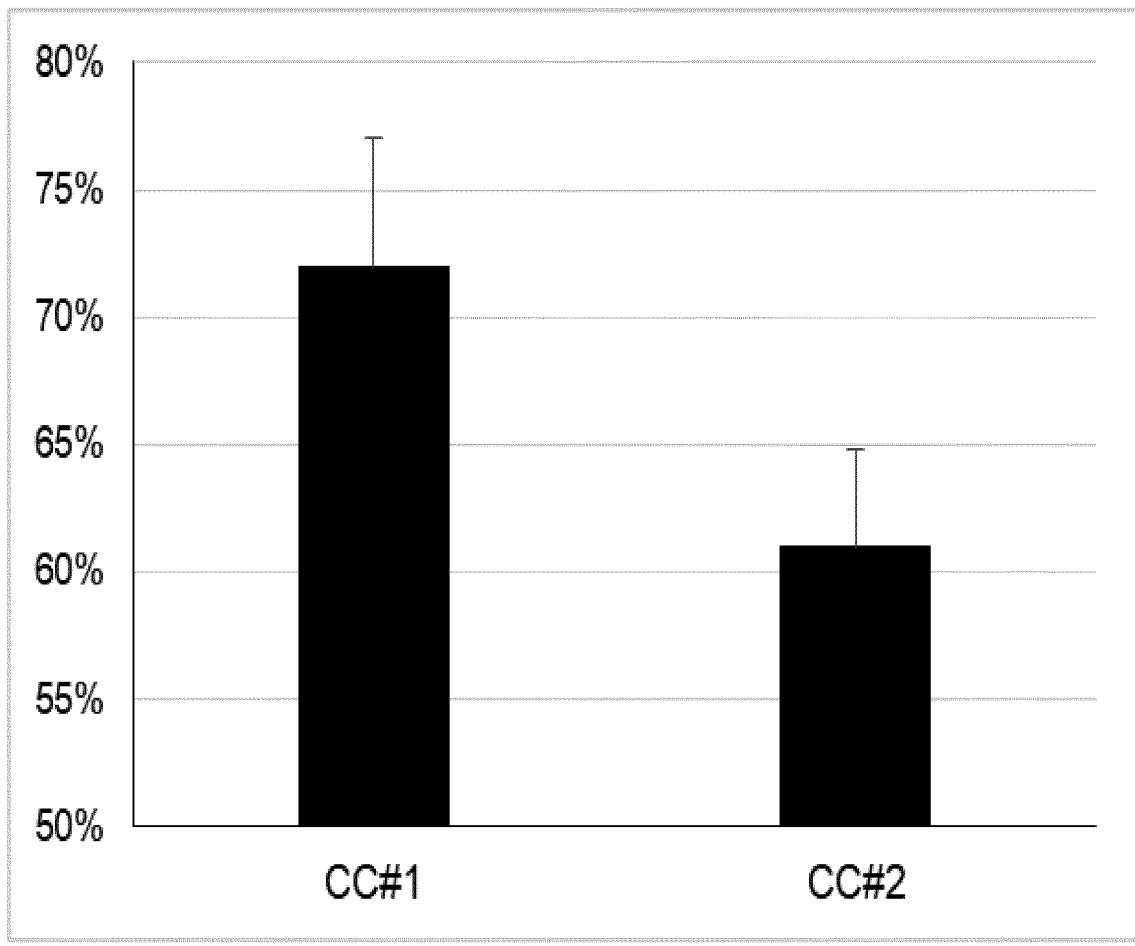

BACTERIAL OIL TREATMENT COMPOSITION FOR HANDLING A DECOMMISSIONED OIL CABLE

FIELD OF THE INVENTION

The invention relates to an improved bacterial oil treatment composition or pool for handling a decommissioned oil cable, which may be laid in particular as part of a power grid in the ground, lakes and sea. The present invention further relates to an adapted or tailored bacteria growth culture medium containing said bacterial oil treatment composition for refurbishing an oil cable and a corresponding use thereof.

BACKGROUND OF THE INVENTION

Since the 1930s, utilities have used oil cables in their power grids, especially for low voltage, medium voltage and high voltage. Oil cables are used in particular in the voltage range of 10 to 500 kV. The oil cables are usually laid in the ground, especially in the soil, lakes and sea.

An oil cable has one or more electrical conductors within an outer shell. For isolating the electrical conductors from each other and from the outer shell, the electrical conductors are surrounded on the one hand by a respective oil-soaked matrix, for example of paper. On the other hand, gaps between the electrical conductors are filled with each other and between the electrical conductors and the outer shell with oil, which is continuously pumped through the oil cable during operation of the oil cable. These spaces thus form an oil channel. The oil in the matrices and the oil in the oil channel cause a particularly uniform electrical insulation, because inhomogeneities of the remaining insulation can be compensated by the typically thin liquid and dielectric oil. Without the oil, uneven performance of the remaining insulation, along with trapped air and/or dirt, could lead to localized increases in electrical field strength with partial discharges that could damage the oil cable.

The oil in an oil cable poses a potential ecological hazard. If an oil cable is damaged, escaping oil can lead to environmental pollution, in particular by the oil getting into the groundwater.

Since about the 1990s, therefore, alternatives to oil cables are increasingly used, such as cables with insulation made of cross-linked polyethylene. Unused oil cables are taken out of service accordingly. The oil can be pumped out of the oil channel. However, oil remains in the matrices. For example, 50% of the oil that is in an oil cable during operation may remain in the dies. Thus, oil cables pose a potential hazard to the environment even after decommissioning. Therefore, for example, in Germany it is legally required to monitor oil cables even after decommissioning, for example electronically and/or hydraulically. In Germany, for example, the Ordinance on Installations for the Handling of Substances Hazardous to Water (AwSV) contains corresponding specifications. Such monitoring can detect damage to an oil cable and thus limit the damage to the environment. However, environmental pollution in the event of damage to an oil cable cannot be ruled out. Furthermore, the monitoring causes significant costs for the public authorities. These costs are no longer useful in decommissioned oil cables. Also, these costs are ongoing costs, which in principle are incurred indefinitely.

It would be conceivable to remove unneeded oil cables from the ground. But if, for example, a road surface has to be opened, this can cost millions. Compared to this, the costs of monitoring are often lower. The opening of a road surface can also cause restrictions for the population, for example due to traffic congestion or noise.

WO 2015/191582 A1 (BIOWISH TECHNOLOGIES INC [US]) relates to microbial compositions and a process for reducing hydrocarbon contamination. The composition for hydrocarbon remediation, comprising a microbial mixture of *Bacillus* and *Pseudomonas* organisms, wherein each of the organisms, in the mixture is individually aerobically fermented, harvested, dried, and ground to produce a powder having a mean particle size of about 200 microns, with greater than about 60% of the mixture in the size range between 100-800 microns. Also disclosed is a process for remediating an oil contaminated substrates comprising: a) grinding the substrate to a particle size less than 1000 microns to produce a ground substrate; b) adding the ground substrate to an aqueous solution comprising a microbial mixture of *Bacillus, Pseudomonas*, and a nitrogen source to produce a solution and c) stirring the solution for up to 72 hours.

KR 2015 0062130 A (UNIV INJE IND ACAD COOPERATION [KR]) relates to a strain *Bacillus pumilus* IJ-1 capable of decomposing oil; and, more specifically, to a method for culturing *Bacillus pumilus* IJ-1 which is capable of decomposing oil and produces a bio surfactant. The strain *Bacillus pumilus* IJ-1 of this invention has excellent capability of decomposing oil such as crude oil, gasoline, kerosene, and diesel and furthermore has capability of producing the bio surfactant. According to the invention, an optimal culture condition for growth of *Bacillus pumilus* IJ-1 and for producing the bio surfactant is defined. The strain *Bacillus pumilus* IJ-1 can be used for preventing oil contamination from being spread and decomposing oil effectively when an oil accident in the sea or soil contamination occurs. Therefore, the strain *Bacillus pumilus* IJ-1 is useful for an environmental industry.

RAPP P. ET AL: "Formation of exopolysaccharides by and partial characterization of a heteropolysaccharide of high molecular weight", APPLIED MICROBIOLOGY AND BIOTECHNOLOGY, vol. 7, no. 1, 1 Mar. 1979, (1979-03-01), pages 67-78, XP035173104, ISSN: 1432-0614, DOI: 10.1007/BF00522480 discloses that polysaccharide formation by *Rhodococcus erythropolis* was studied using lower mono-, di- and trihydric alcohols, sugars and n-alkanes as carbon sources. Cultural conditions of the organism were examined with regard to polysaccharide production. It was demonstrated that a glycerol substrate, a 30° C. incubation temperature and a pH of 7.5 were optimal cultural conditions for polysaccharide formation. Addition of penicillin G in the decelerating growth phase increased the polysaccharide concentration in the culture filtrate to 3 0.1 g/l. One of the main extracellular heteropolysaccharides formed by *Rhodococcus erythropolis* consisted of glucose and mannose in the molar ratio 1:1, a small portion of protein and a trace of glucosamine.

DE 20 2019 104226 U1 (TIBIO SAGL [CH]) discloses means and methods for degradation of cable oil, using a bacterial oil treatment composition comprising *B. subtilis, B. licheniformis* and *R. rhodochrous*, and using a medium growth medium therefore. In particular this document discloses a device for the remediation or disposal of an oil cable, comprising: a storage container for a bacterial liquid, a pump and pipes for introducing the bacterial liquid into an oil channel of the oil cable and for removing the bacteria-containing liquid from the oil channel, and a collecting container for receiving the bacteria-containing liquid after removal from the oil channel, wherein the device further comprises an emulsion processing module for removing the foam and an automatic separation unit for separating the oil from the bacteria-containing liquid.

MOLNAR M. ET AL: "Enhanced biodegradation of transformer oil in soils with cyclodextrin—from the laboratory to the field", BIODEGRADATION, vol. 16, no. 2, 1 Mar. 2005 (2005-03-01), pages 159-168, XP019231900, ISSN: 1572-9729, DOI: 10.1007/S10532-004-4873-0, discloses the use of cyclodextrins for the intensification of bioremediation by improving the mobility and bioavailability of contaminants. The role of randomly methylated β-cyclodextrin in the bioremediation of soils contaminated with transformer oil was studied both in bench scale bioreactors and through field experiments. The aims of this research were to (a) establish the scientific background of a cyclodextrin-based soil bioremediation technology, (b) demonstrate its feasibility and effectiveness in the field, and (c) develop an integrated methodology, consisting of a combination of physical, chemical, biological and ecotoxicological analytical methods, for efficiently monitoring the technology performances. The stepwise increasing scale of the experiments and the application of the integrated analytical methodology supported the development of a scientifically established new technology and the identification of the advantages and the limitations of its application in the field. At each phase of the study, randomly methylated β-cyclodextrin was found to significantly enhance the bioremediation and detoxification of the transformer oil-contaminated soils employed by increasing the bioavailability of the pollutants and the activity of indigenous microorganisms.

There is however a need for a way of dealing with oil cables that are no longer required, on the one hand protects the environment and on the other hand are as cost-effective as possible.

There is already a solution in the field of biodegradation of dielectric oils using specialized bacteria specially selected. This solution solves problems of contamination or pollution, in offering a system for the treatment of oil-filled cables. The ODB (Oil degradation by bacteria) system allows the treatment of oil-filled cables directly in situ, without the need for expensive and complex operations of cable removal. The principle is based on repeated injections into the cable of bacteria feeding solely on dielectric oil. This method has been successfully tested on sub-lacustrine cables ranging from 1 to 2 kilometers in length and 50 to 70 meters in altitude: the results showed that 96% of the oil contained in the cable was removed after 6 months of treatment (the remaining 4% is intimately contained in the paper, reducing to zero any risk of flow pollution). The original technique is carried out in several stages. The bacteria are injected into the cables by pumping and diffuse into the matrix containing the insulating oil. These are specially selected to actively degrade the oil and to produce bio-surfactants, so-called natural soaps that promote the release of oil out of the matrix. After a treatment lasting 4 to 6 months (depending on the situation) and punctuated by periodic checks, the oil is finally extracted from the cable by pumping. This system uses bacteria of natural origin contained in sealed containers, which are neither pathogenic nor GMO. They pose no danger, neither for the employees involved on the site, nor for the environment.

However, there would be a need to increase the treatment speed while keeping or even improving the efficacy in removing the oil contained in the cable. It is also a need to treat longer sections of oil cables.

Another risk during bioremediation is the formation of water-soluble and toxic forms of oxidized heavy metals, in particular copper and lead. Indeed, since the conditions in the cable become rapidly anaerobic, the bacteria could use the heavy metals as acceptors of electrons for the cellular respiration with the consequent formation of oxidized ionic forms.

On this basis, it is an object of the present invention to solve the technical problems described in connection with the prior art or at least to reduce them. In particular, it is provided an improved bacteria composition or pool for dealing with a decommissioned oil cable and a tailored bacteria medium containing said bacteria composition for refurbishing an oil cable, which allows dealing with a longer oil cable, on the one hand the environment is protected and on the other hand is cost effective.

BRIEF DESCRIPTION OF THE INVENTION

These objects are achieved by an improved bacterial oil treatment composition or pool for handling a decommissioned, laid in a floor oil cable. Also, this object is achieved by using a tailored bacteria growth medium containing said bacterial oil treatment composition for refurbishing an oil cable. The features listed individually in the claims can be combined with each other in any technologically meaningful manner and can be supplemented by explanatory terms from the description, with further embodiments of the invention being shown.

In particular, one of the objects of the present invention is to provide a bacterial oil treatment composition for the biodegradation of oil in a decommissioned oil cable and/or for the production of bio-surfactants in a decommissioned oil cable, wherein said bacterial oil treatment composition comprises a bacteria community consisting of 20% of *Pseudomonas fluorescens,* 40% of *Bacillus subtilis,* 30% of *Bacillus licheniformis* and 10% of *Rhodococcus rhodochrous.*

Another object of the present invention is to provide a bacterial growth culture medium (herein referred as ODB medium) for hosting the bacterial oil treatment composition according to the invention, comprising water and standard salts selected from the group comprising NH4Cl, NH4NO3, K2HPO4, KH2PO4, Na2HPO4, MgSO4*7H2O, FeSO4*7H2O and NaNO3; wherein said bacterial growth medium further comprises:

a) an organic started mix selected from the group comprising yeast extracts, malt extract, cane molasses and methyl-β-cyclodextrin;
b) a biocompatible antifoam mix selected from the group comprising Na2EDTA, polydimethylsiloxane, simethicone and rapeseed oil; and
c) a mix of essential amino-acids selected from the group of branched-chain amino acid comprising: Na Leucine, Na Valine, Na Isoleucine; in addition to Na Glutamate at a ratio 1:1:1:1 and a mix of nitrogen fertilizers.

A further object of the invention is to provide a bacterial oil treatment containing liquid for the biodegradation of oil in a decommissioned oil cable and/or for the production of bio-surfactants in a decommissioned oil cable, wherein said bacterial oil treatment containing liquid comprises the bacterial oil treatment composition according to the invention and the bacterial growth culture medium according to the invention.

Still another object of the invention is the use of the bacterial oil treatment containing liquid, for the biodegradation of oil in a decommissioned oil cable and/or for the production of bio-surfactants in a decommissioned oil cable, wherein said bacterial oil treatment containing liquid is capable of removing the oil contained in said decommissioned oil cable.

Other objects and advantages of the invention will become apparent to those skilled in the art from a review of the ensuing detailed description, which proceeds with reference to the following illustrative drawings, and the attendant claims.

BRIEF DESCRIPTION OF THE FIGURES

FIG. 3: shows the comparison between strains and the bacterial community (co-culture), all in the ODB media of the invention with 2% dielectric oil for 2 weeks at 30° C. under shaking (150 rpm). Results are expressed as % of degraded oil compared to a control (ODB media+oil without bacteria).

FIG. 4: shows the comparison between the ODB media of the invention, Luria Broth and a standard media described in the literature for the degradation of dielectric oil (Molnar et al. 2005). Results are expressed as % of degraded oil compared to a control (ODB media+oil without bacteria).

FIG. 5: illustrates a GC-FID chromatogram of dielectric oil treated 4-days with the ODB co-culture in standard mineral media (black arrow) and ODB media (white arrow) with 2% oil. The chromatogram indicated by a white arrow shown smaller fragments (shorter retention time) compared to the chromatogram indicated by a black arrow, proving that oil is degraded faster.

FIG. 6: shows the concentration of dissolved copper (black) and lead (grey) in the media after the treatment of an oil-filled electric cable for 4 months (laboratory scale).

FIG. 7: shows a comparison between the co-culture with *P. fluorescens* (CC #1) and without *P. fluorescens* (CC #2), all in the ODB media with 2% dielectric oil for 2 weeks at 30° C. under shaking (150 rpm).

DETAILED DESCRIPTION OF THE INVENTION

Figure 1:
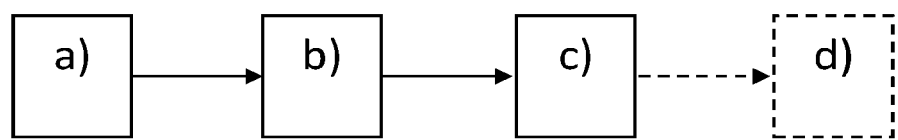
FIG. 1: shows a flowchart of a method according to the invention for the renovation of an oil cable.

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control.

Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

As used in the specification and claims, the singular forms "a", "an" and "the" include plural references unless the context clearly dictates otherwise.

The term "an effective amount" refers to an amount necessary to obtain a physiological effect. The physiological effect may be achieved by one application dose or by repeated applications. The dosage administered may, of course, vary depending upon known factors, such as the physiological characteristics of the particular composition; the age, health and weight of the subject; the nature and extent of the symptoms; the kind of concurrent treatment; the frequency of treatment; and the effect desired and can be adjusted by a person skilled in the art.

It is an object of the invention to provide a bacterial oil treatment composition for the biodegradation of oil in a decommissioned oil cable and/or for the production of bio-surfactants in a decommissioned oil cable, wherein said bacterial oil treatment composition comprises a bacteria community consisting of 20% of *Pseudomonas fluorescens*, 40% of *Bacillus subtilis*, 30% of *Bacillus licheniformis* and 10% of *Rhodococcus rhodochrous*. Said bacterial oil treatment composition is capable of removing or clearing out the oil contained in said decommissioned oil cable.

The bacteria community consists of 20% of *Pseudomonas fluorescens*, 40% of *Bacillus subtilis*, 30% of *Bacillus licheniformis* and 10% of *Rhodococcus rhodochrous*.

By an "oil cable" it is meant a cable that has at least one electrical conductor and in any case an oil insulation. In particular, the bacterial oil treatment composition can be applied to oil cables in which the at least one electrical conductor is surrounded by a respective oil-soaked matrix, for example of paper. Gaps between different ones of the matrices and/or between the at least one matrix and an outer shell of the oil cable form the oil channel. Through this, a particularly low-viscosity and dielectric oil is usually pumped during operation of the oil cable.

The bacterial oil treatment composition of the invention is preferably applied to unneeded, decommissioned oil cables.

The bacterial strains mentioned occur in nature and are known per se. In particular, bacteria of these strains can dissolve oil, for example, from matrices of an oil cable. The bacterial oil treatment composition of the invention may contain other bacteria or substances.

The mentioned bacteria of the invention are those of risk group 1 i.S.v. German standard § 3 (1) No. 1 BioStoffV. These are bio-substances that are unlikely to cause disease in humans. If the oil cable is damaged when carrying out the invention, no or only very little damage to the environment will occur even if the bacteria are released.

Also provided is the use of the bacterial oil treatment composition of the invention for the biodegradation of oil cable and/or for the production of bio-surfactants in a decommissioned oil cable, wherein said bacterial oil treatment composition is capable of removing the oil contained in said decommissioned oil cable, and wherein said bacterial oil treatment composition comprises a bacteria community consisting of 20% of *Pseudomonas fluorescens*, 40% of *Bacillus subtilis*, 30% of *Bacillus licheniformis* and 10% of *Rhodococcus rhodochrous*.

Another object of the invention is to provide a bacterial growth culture medium for hosting the bacterial oil treatment composition of the invention. The bacterial growth medium comprises water and standard salts selected from the group comprising $NH_4Cl$, $NH_4NO_3$, $K_2HPO_4$, KH2PO4, Na2HPO4, MgSO4*7H2O, FeSO4*7H2O and NaNO3; wherein said bacterial growth medium further comprises:
a) an organic started mix selected from the group comprising yeast extracts, malt extract, cane molasses and methyl-β-cyclodextrin;
b) a biocompatible antifoam mix selected from the group comprising Na2EDTA, polydimethylsiloxane, simethicone and rapeseed oil; and
c) a mix of essential amino-acids selected from the group of branched-chain amino acid comprising: Na Leucine, Na Valine, Na Isoleucine; in addition to Na Glutamate at a ratio 1:1:1:1 and a mix of nitrogen fertilizers.

According to an embodiment of the invention, the mix of nitrogen fertilizers is selected from the group comprising: urea, uric acid and water soluble lecithin at a ratio 2:1:1.

According to a further embodiment, the composition of 1 litre of organic started mix comprises:
1-100 g/L of yeast extract;
1-100 g/L of malt extract;
1-300 g/L of cane molasses; and
0.1-10/L of methyl-β-cyclodextrin.

Preferably, the composition of 1 litre of organic started mix comprises:
40 g/L of yeast extract;
40 g/L of malt extract;
100 g/L of cane molasses; and
1 g/L of methyl-β-cyclodextrin.

According to another embodiment, the composition of 1 litre of biocompatible antifoam mix comprises:
1-2000 mg/L of Na2EDTA;
20-500 g/L of polydimethylsiloxane;
0.1-200 g/L of simethicone; and
10-300 mL/L of rapeseed oil.

Preferably, the composition of 1 litre of biocompatible antifoam mix comprises:
500 mg/L of Na2EDTA;
200 g/L of polydimethylsiloxane;
50 g/L of simethicone; and
100 mL/L of rapeseed oil.

According to the invention, the bacterial growth culture medium of the invention comprises a mix of essential amino-acids and nitrogen fertilizers, wherein the composition of 1 litre of mix of essential amino-acids and nitrogen fertilizers comprises:
1-500 mg/L of the mix of branched-chain amino acid;
1-500 mg/L of Na glutamate;
1-500 mg/L of uric acid;
1-500 mg/L of urea; and
1-500 mg/L of water soluble lecithin.

According to a preferred embodiment, 1 litre of the bacterial culture growth medium of the invention comprises:
0.05-8 g/L of the bio-compatible antifoam mix;
5-200 g/L of the organic started mix;
0.5-20 g/L of the mix of essential amino-acids and nitrogen fertilizers, and wherein the final volume is adjusted to 1 litre with water and standard salts selected from the group comprising NH4Cl, NH4NO3, K2HPO4, KH2PO4, Na2HPO4, MgSO4*7H2O, FeSO4*7H2O and NaNO3.

However in view of specific uses, additional standard salts known by the skilled person may be added to the bacterial growth culture medium of the invention without imparting from the teaching of the present invention.

Preferably, the concentration of standard salts consists of:
NH4Cl at 2.0 g/l; NH4NO3 at 2.0 g/L; K2HPO4 at 4.0 g/L; KH2PO4 at 4.0 g/L; Na2HPO4 at 0.5 g/L; MgSO4*7H2O at 1.0 g/L; FeSO4*7H2O at 0.2 g/L and NaNO3 at 1 g/L.

An important risk during bioremediation is the formation of water-soluble and toxic forms of oxidized heavy metals, in particular copper and lead. Indeed, since the conditions in the cable become rapidly anaerobic, the bacteria could use the heavy metals as acceptors of electrons for the cellular respiration with the consequent formation of oxidized ionic forms. Therefore, the bacterial growth medium (also referred herein as culture medium) of the invention contains alternative acceptors of electrons to compensate the absence of dissolved oxygen. This is successfully obtained by adding essential amino-acids and nitrogen-containing organic compounds to reduce the oxidative stress of bacteria, and by further adding standard mineral salts—in particular those containing NO3. The addition of antifoam plays also an important role, by reducing the formation oil-in-water emulsion and facilitating the chemical exchange between bacteria and the growth culture medium.

It is another object of the invention to provide a bacterial oil treatment containing liquid for the biodegradation of oil in a decommissioned oil cable and/or for the production of bio-surfactants in a decommissioned oil cable, wherein said bacterial oil treatment containing liquid comprises the bacterial oil treatment composition of the invention and the bacterial growth culture medium according to the invention.

According to an embodiment of the invention, said bacterial oil treatment containing liquid comprises 2 g/L (wet weight) of the bacterial oil treatment composition of the invention.

Preferably, the bacterial oil treatment containing liquid has a water content in the range of 60 to 80%.

It has been found that bacteria can solve oil in an oil cable particularly well at a water content in said range. The proportion of water can in particular contribute to make the bacterial oil treatment containing liquid sufficiently thin, so that the bacterial oil treatment containing liquid can penetrate sufficiently, for example, in the matrices of the oil cable. In addition, the water can serve as a livelihood for bacteria. A higher water content could cause the bacteria to have only a weak effect on the oil in the oil cable.

According to an embodiment of the invention, the bacterial oil treatment containing liquid further comprises a defoamer.

The bacterial oil treatment containing liquid can form a foam in particular due to surfactants. This may affect the ability of bacteria to dissolve oil from, for example, dies of an oil cable. This is particularly because the foam can affect contact between the bacteria in the bacteria-containing fluid (or liquid) and the oil to be dissolved. As a result, the time required to carry out the method described can be increased. Foaming may also lead to an unpleasant odor development. By adding a defoamer can be counteracted the disadvantages mentioned. As a defoamer is in particular a so-called antifoam into consideration.

The defoamer is contained in the bacterial oil treatment containing liquid at least in step a), that is to say when the bacteria-containing liquid is introduced into the oil channel. This can change as the process progresses.

Preferably, the defoamer is added every 4 to 6 weeks of the bacterial oil treatment containing liquid stored in a reservoir. If the bacteria-containing liquid collected after removal from the oil passage and after separation of the oil by an oil separator in a collection container, the bacterial oil treatment containing liquid is preferably also added to the sump an antifoam. Thus, the bacterial oil treatment containing liquid can be reused particularly well, even if not all the oil was removed from the bacterial oil treatment containing liquid by the oil separator.

According to another embodiment of the invention, the bacterial oil treatment containing liquid further comprises oxygen.

Also provided is the use of the bacterial oil treatment containing liquid according to the invention, for the biodegradation of oil in a decommissioned oil cable and/or for the production of bio-surfactants in a decommissioned oil cable, wherein said bacterial oil treatment containing liquid is capable of removing the oil contained in said decommissioned oil cable.

FIG. 1 illustrates a typical method of using the bacterial oil treatment containing liquid of the invention. According to a preferred embodiment of the method, the bacteria oil treatment containing liquid in step a) contains the bacterial community strains and particular percentages as mentioned above. However, in the course of the procedure this can change, for example by the death of bacteria.

According to another preferred embodiment of the invention, a composition of the bacterial oil treatment containing liquid is selected in dependence on properties of oil to be removed in the oil cable. The invention described is intended to be applied to existing oil cables. These oil cables were partially laid underground many decades ago. It is therefore to be expected that different oil cables have different materials, in particular with regard to the outer shell and/or the matrices. Also, various types of oil may have been used. All of this can affect how efficiently the oil still contained in an oil cable can be removed with a particular bacterial fluid. Therefore, according to the present embodiment, it is preferable to determine the properties of the oil to be removed in the oil cable, preferably also other materials of the oil cable. Based on this, the composition and bacterial amount of the bacterial oil treatment containing liquid can be selected. In particular, the proportion and type of bacteria used can be selected.

As explained above, the bacterial oil treatment containing liquid has a water content in the range of 60 to 80%.

The said water content is present in step a) (see FIG. 1), that is to say when the bacterial oil treatment containing liquid is introduced into the oil channel. In the further course of the process, the water content may change. In particular, a significant amount of oil may be added resulting from the oil being removed from the oil cable.

According to a further preferred embodiment, the bacterial oil treatment containing liquid in step a) contains a salt.

Many oil cables contain metals and/or PCBs. These materials can have a negative impact on the bacteria. In particular, these materials may affect the ability of bacteria to dissolve oil from, for example, dies of an oil cable. It has been found that the addition of salt can counteract this. As a salt is especially sodium chloride into consideration.

The salt is contained in the bacterial oil treatment containing liquid at least in step a), that is to say when the bacterial oil treatment containing liquid is introduced into the oil channel. This can change as the process progresses.

According to a further preferred embodiment of the invention, oxygen is added to the bacterial oil treatment containing liquid during storage outside the oil channel.

Figure 2:
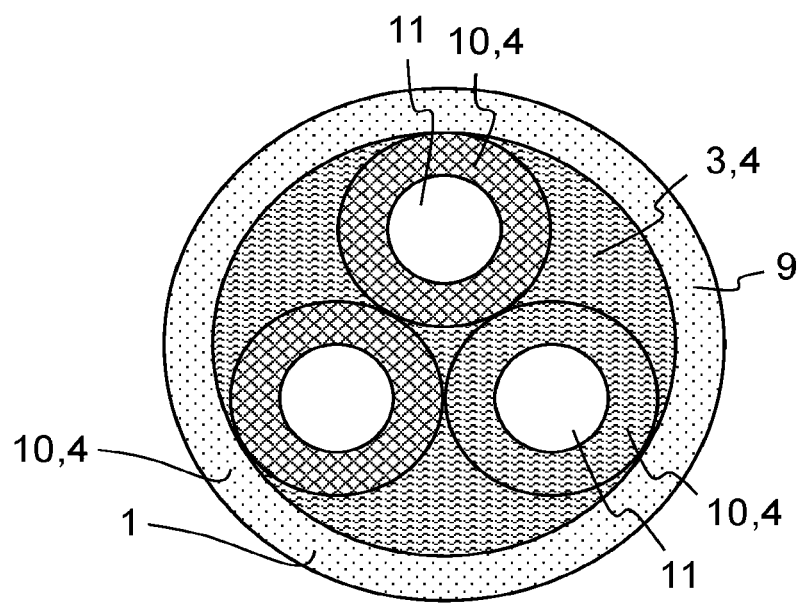
FIG. 2: illustrates a first cross-sectional view of an oil cable, which can be rehabilitated according to the invention.

The bacterial oil treatment containing liquid can be removed from a reservoir in step a) and introduced into the oil passage of the oil cable (see FIG. 2). Preferably, the reservoir contains bacterial oil treatment containing liquid for more than one rinse of an oil cable and/or for the renovation of more than one oil cable. Accordingly, a portion of the bacterial oil treatment containing liquid is stored in the reservoir, while another part is in the oil passage of one or more oil cables. Generally, the bacterial oil treatment containing liquid is preferably stored in the reservoir before performing step a). The bacterial oil treatment containing liquid stored in the reservoir is mixed with oxygen according to this embodiment. This can increase the activity of the bacteria.

According to the invention, a typical method for the remediation of an oil cable comprises:

a) introducing a bacterial oil treatment containing liquid into an oil passage of the oil cable, b) allowing the bacterial oil treatment containing liquid to rest in the oil channel, and c) removing the bacterial oil treatment containing liquid (or bacterial fluid) from the oil channel.

With the described method, an oil cable can be rehabilitated.

With the described method such oil can be removed from the oil cable, which is contained for example in the matrices. Indeed, 90% of the oil contained in the matrix and even more can be removed. In view of this small quantity of oil remaining in the cable, it is possible to leave the oil cable in the ground without the need to monitor the oil cable for legal reasons. As a result, public authorities can save significant costs for monitoring oil cables that are no longer needed. The costs associated with the treatment may be small compared to the cost of monitoring. This is especially true because the monitoring of an oil cable may last indefinitely.

Furthermore, with the described method and invention, the environment can be particularly well protected. This is due to the fact that no oil or only very little oil is released into the environment even if the oil cable has been damaged, because the oil has been almost completely removed from the oil cable. Besides, the portion of the oil which cannot be removed is unlikely to be released into the environment even if the oil cable is damaged. The oil can be removed from the oil cable by the bacterial oil treatment containing liquid of the invention. This is based on the knowledge that bacteria can be used to reduce oil, for example, in paper matrices. The bacterial oil treatment containing liquid comprises a solution of the bacterial oil treatment composition of the invention. As the solvent, water is preferable.

The steps a) to c) of the method described are preferably carried out in the order given. In this case, step b) begins after completion of step a) and step c) begins after completion of step b).

In step a) of the described method, the bacterial oil treatment containing liquid is introduced into the oil passage of the oil cable. This is done for example by pumping the bacterial oil treatment containing liquid from a reservoir into the oil passage, in particular until the oil passage is completely filled.

Subsequently, the bacterial oil treatment containing liquid is rested in step b) in the oil passage. This means that the bacterial oil treatment containing liquid is not actively moved during the duration of step b), for example by a pump. By resting, the bacteria in the bacterial oil treatment containing liquid can act on the oil contained, for example, in the matrices.

After resting, the bacterial oil treatment containing liquid, which now also has an oil content, is removed from the oil channel according to step c). This can be done by pumping the bacterial oil treatment containing liquid via a pipe at one end of the oil cable from the oil passage into a collection container. This can be done by sucking with a pump at this end of the oil cable and/or by introducing at the other end of the oil cable a fluid into the oil channel which pushes the bacterial oil treatment containing liquid out of the oil channel. In particular, this fluid may again be a bacterial oil treatment containing liquid which is introduced into the oil channel according to a further implementation of step a). Thus, several rinses can be done in a row.

After removal, the bacterial fluid may be discarded or reprocessed. Preferably, the oil contained in the bacterial oil treatment containing liquid which has been removed from the oil cable is separated from the bacterial oil treatment containing liquid, for example by an oil separator. Subsequently, the bacterial oil treatment containing liquid can be reused.

The bacterial oil treatment containing liquid is preferably introduced into a first end of the oil cable according to step a) and removed from a second end of the oil cable according to step c). Alternatively, it is preferred that bacterial oil treatment containing liquid according to step c) was taken from the oil cable at the same end at which the bacterial oil treatment containing liquid was also introduced into the oil cable according to step a). This is particularly advantageous if one of the ends of the oil cable is difficult to access.

Through the steps a) to c) oil can be removed from the oil cable. In that regard, the residual oil content in the oil cable can be reduced. Depending on the effectiveness of steps a) to c) on the oil contained in the oil cable and depending on the result on the residual oil content, a one-time execution of steps a) to c) may suffice.

Alternatively, steps a) to c) may be repeated cyclically.

By repeatedly performing steps a) to c), a particularly low residual oil content can be achieved, even if the oil in the oil cable is difficult to remove. Each cycle can be referred to as a rinse.

The treatment may be terminated after a predetermined number of cycles. Preferably, steps a) to c) are carried out in each case 10 to 20 times (10 to 20 cycles).

Alternatively, the method according to another preferred embodiment further comprises:

d) measuring an oil content of the bacterial oil treatment containing liquid taken from the oil channel according to step c).

Steps a) to d) are repeated cyclically until the determined oil content in step d) has reached a predetermined limit.

In this embodiment, the process is preferably carried out until a desired residual oil content has been reached, for example said content is less than 5%. In particular, the procedure may be terminated when a legal threshold for monitoring has been reached so that once the procedure has been completed, monitoring of the oil cable is no longer required.

As a measure of the residual oil content, the proportion of oil in accordance with step c) taken from the oil channel bacterial oil treatment containing liquid can be used. Under the reasonable assumption that the bacterial oil treatment containing liquid under the same conditions can always remove the same proportion of the remaining oil from the oil cable, it can be concluded from the proportion of oil from the bacterial oil treatment containing liquid taken from the oil channel according to step c) how much oil is still present in the oil cable.

The proportion of oil in the bacterial oil treatment containing liquid removed from the oil channel in accordance with step c) can be determined, for example, by measuring the amount of oil separated by an oil separator from the bacterial oil treatment containing liquid removed from the oil channel.

Preferably, the determination of the oil content of the bacterial oil treatment containing liquid taken from the oil channel in accordance with step c) takes place automatically, in particular with the aid of a control device.

In addition, at least one further parameter of the method is preferably selected based on the properties of the oil to be removed from the oil cable, in particular also on the properties of other materials in the oil cable. Particularly suitable parameters of this type are: the duration of step b), the pressure with which the bacterial oil treatment containing liquid is introduced into the oil channel in step a) and/or the time the bacterial oil treatment containing liquid will stay in the oil channel in step b) and the number of cycles of steps a) to c).

According to a further preferred embodiment of the method, the bacterial oil treatment containing liquid is introduced at a pressure in the range of 1 to 5 bar in step a) into the oil channel and/or rested in step b) in the oil channel.

Preferably, said pressure is present at the end of step a). If the oil cable is closed by a valve at the time, for example, the pressure can be maintained for the duration of step b). Unavoidable pressure losses, such as small leaks, should be disregarded. It has been found that oil can be dissolved particularly well at a pressure in the mentioned range, for example, especially from the matrices in the oil cable. Particularly preferably, the pressure is in the range between 2 and 4 bar.

According to a further preferred embodiment of the method, step b) is carried out over a period of at least 3 days.

During rest, bacteria in the bacterial oil treatment containing liquid can dissolve oil from, for example, dies in the oil cable. The bacteria can enter into the matrices to get to the oil. This process can take several days. Therefore, it is preferred that step b) be performed for at least 3 days. Particularly preferred is the implementation of step b) over a period of at least 5 days. The upper limit is a duration of 20 days, in particular of 10 days.

If step b) is carried out over a period of, for example, 7 to 10 days, and if steps a) to c) are carried out in each case 10 to 20 times, the method lasts altogether between 70 and 200 days. The process typically has a duration of a few months.

As a further aspect of the invention, a use of the bacterial oil treatment containing liquid for refurbishing an oil cable is presented.

The particular advantages and design features as described above are applicable to the described use and transferable.

As a further aspect of the invention, there is provided a method of handling a decommissioned oil-laid oil conduit by removing oil from the oil conduit located in the oil conduit and leaving the oil conduit in the ground.

In particular, the oil is removed from the oil cable using the bacterial oil treatment containing liquid of the invention.

It is preferred that a proportion of at least 90% of oil, particularly preferably of at least 95%, be removed.

By using the bacterial oil treatment containing liquid to remove oil from an oil cable, it is possible to remove oil from an oil cable and leave the oil cable in the ground. Most preferably, the oil cable is left in the ground without being monitored.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practising the present invention and are not intended to limit the scope of the invention.

EXAMPLES

Example 1

Preparation of the Organic Started Mix

The organic started mix contains easily assimilable organic matter to reduce the lag phase when bacteria are in diluted in fresh media. A typical recipe is: 40 g/L yeast extract (1-100 g/L) and 40 g/L malt extract (1-100 g/L) are diluted in 500 mL of water, then 100 g/L of cane molasses (1-300 g/L) is added and the volume is completed to 9 mL with distilled water. The solution is sterilized at 121° C. for 20 min, then 1 g/L methyl-β-cyclodextrin (0.1-10 g/L) is added and the volume is completed to 1000 mL with distilled water.

Example 2

Preparation of the Bio-Compatible Antifoam Mix

The mix is prepared by dissolving 500 mg/L $Na_2EDTA$ (1-2000 mg/L) in 500 mL distilled water at pH 9.0 (with NaOH). Then, 200 g/L polydimethylsiloxane (20-500 g/L) and 50 g/L Simethicone (0.1-200 g/L) are added. The solution is then exposed to ultra-sounds (ultra-sonic bath) for 30 min to obtain a stable emulsion, then 100 mL/L of rapeseed oil (10-300 mL/L) are added and the solution is further sonicated for 30 min to obtain a stable emulsion.

Example 3

Preparation of the Mix of Essential Amino-Acids and Nitrogen Fertilizers

The latter mix is prepared by mixing Na Leucine, Na Valine, Na Isoleucine and Na Glutamate (powders) in a ration 1:1:1:1, then mixed 1:1 with a powder containing urea, uric acid and powdered water soluble lecithin in a ration 2:1:1.

| Mix of Branched-chain amino acid | 1-500 mg/L |
| Uric Acid | 1-500 mg/L |
| Urea | 1-500 mg/L |
| Lecithin | 1-500 mg/L |
| Na glutamate | 1-500 mg/L |

Example 4

Bacterial Media Preparation: (ODB Media According to the Invention)

The following salts are diluted in 850 mL of tap water (non-sterile): $NH_4Cl$ 2.0 g/l, $NH_4NO_3$ 2.0 g/L, $K_2HPO_4$ 4.0 g/L, $KH_2PO_4$ 4.0 g/L, $Na_2HPO_4$ 0.5 g/L, $MgSO_4 \cdot 7H_2O$ 1.0 g/L, $FeSO_4 \cdot 7H_2O$ 0.2 g/L (Ferrous sulfate heptahydrate, Iron(II) sulfate heptahydrate), $NaNO_3$ 1 g/L. Then, 0.5 mL of the bio-compatible antifoam mix (0.1-5 mL) according to example 2 and 5.0 g/L of the mix of essential amino-acids and nitrogen fertilizers (0.5-20 g/L) according to example 3. Immediately before the addition of 2 g/L (wet weight) bacteria co-culture from agar plates (0.2-5 g/L), 100 mL of the organic started mix according to example 1 are added (10-300 mL/L). Final volume is adjusted to 1000 mL with tap water.

Example 5

Preparation of the Standard Mineral Media (for Experimental Comparisons):

The following salts are diluted in 850 mL of tap water (non-sterile): $NH_4Cl$ 2.0 g/l, $NH_4NO_3$ 2.0 g/L, $K_2HPO_4$ 4.0 g/L, $KH_2PO_4$ 4.0 g/L, $Na_2HPO_4$ 0.5 g/L, $MgSO_4 \cdot 7H_2O$ 1.0 g/L, $FeSO_4 \cdot 7H_2O$ 0.2 g/L, $NaNO_3$ 1 g/L. Then, 2 g/L (wet weight) bacteria co-culture from agar plates are added and final volume adjusted to 1000 mL with tap water.

Example 6

Comparative Data and Results

1. FIG. 3 shows the comparison between separate individual strains and the bacterial community (co-culture of the invention, i.e. the bacterial oil treatment composition), all in the ODB media (i.e. the bacterial growth medium of the invention) with 2% dielectric oil for 2 weeks at 30° C. under shaking (150 rpm). Results are expressed as % of degraded oil compared to a control (ODB media+oil without bacteria). These experiments showed that oil degradation efficiencies of each bacteria strain alone are comparable (comprised by 40 to 55% of degraded oil), whereas the oil degradation efficiency of the co-culture namely the bacterial oil treatment composition increases significantly (+30% to 15%).

2. FIG. 4 shows the comparison between the ODB media (the bacterial growth medium of the invention), Luria Broth and a standard media described in the literature for the degradation of dielectric oil (Molnar et al. 2005; Molnar, M., L. Leitgib, K. Gruiz, E. Fenyvesi, N. Szaniszlo, J. Szejtli, and F. Fava. 2005. "Enhanced biodegradation of transformer oil in soils with cyclodextrin—from the laboratory to the field." Biodegradation 16 (2): 159-168. https://doi.org/10.1007/s10532-004-4873-0. <Go to ISI>://WOS:000226505200007). Results are expressed as % of degraded oil compared to a control (ODB media+oil without bacteria).

Conclusions:

Oil degradation by bacteria causes the fragmentation and oxidation of the hydrocarbon chains. The ODB media was developed to increase this process and contains some key elements helping the biodegradation in the micro-aerobic and anaerobic environment, in particular into the electric cables during the bio-decontamination process. Applicants proved that the media according to the invention helps the degradation of oil as shown in FIG. 5.

3. FIG. 5 illustrates a GC-FID (Gas Chromatography-Flame Ionization Detector) chromatogram of dielectric oil treated 4-days with the ODB co-culture in standard mineral media (black arrow) and ODB media (white arrow) with 2% oil.

Results and Conclusions:

The chromatogram indicated by a white arrow shown smaller fragments (shorter retention time) compared to the chromatogram indicated by a black arrow, proving that oil is degraded faster.

A major challenge working in micro-aerobic and anaerobic environments is to avoid the oxidation of metals (acting as alternative electron acceptor for the cellular respiration of bacteria). The ingredients of the bacterial growth media of the invention help to reduce the oxidation of copper and lead, the two main metals present in electric cables.

4. FIG. 6 shows the concentration of dissolved copper (black) and lead (gray) in the media after the treatment of an oil-filled electric cable for 4 months (laboratory scale). These experiments showed that the production of ionic forms of lead and copper (dissolved elements)—that is a side-effect of the biodegradation—decreases using the ODB media according to the invention compared to standard media, thanks to the presence in the ODB media (i.e. the bacterial oil treatment containing liquid of the invention) of alternative acceptors of electron for cellular respiration.

5. FIG. 7 shows a comparison between the co-culture with P. fluorescens (CC #1) and without P. fluorescens (CC #2), all in the ODB media with 2% dielectric oil for 2 weeks at 30° C. under shaking (150 rpm). Results in Table 1 are expressed as % of degraded oil compared to a control (ODB media+oil without bacteria).

Composition of the Co-Cultures:

TABLE 1

| CC#1 | % | CC#2 | % |
| --- | --- | --- | --- |
| Bacillus subtilis | 20% | Bacillus subtilis | 40% |
| Bacillus licheniformis | 40% | Bacillus licheniformis | 40% |
| Rhodococcus rhodochrous | 30% | Rhodococcus rhodochrous | 20% |
| Pseudomonas fluorescens | 10% | | |

In the co-culture containing P. fluorescens a 10% decrease on oil content in the media is observed compared to the co-culture without P. fluorescens, confirming that this strain plays a key role in the degradation of dielectric oil. This is proof of a synergistic effect due the addition of P. fluorescens to a co-culture without P. fluorescens.

LIST OF REFERENCE NUMBERS

1 Oil cable
3 oil passage
4 oil
9 outer shell
10 matrix
11 electrical conductors

The invention claimed is:

1. A liquid for the biodegradation of dielectric oil in a decommissioned oil cable and/or for the production of bio-surfactants in a decommissioned oil cable, the liquid comprising:

bacterial community consisting of, with respect to percent (%) total bacteria in the bacterial community, 20% of Pseudomonas fluorescens, 40% of Bacillus subtilis, 30% of Bacillus licheniformis and 10% of Rhodococcus rhodochrous; and a bacterial growth culture medium comprising:
water;
standard salts selected from the group consisting of NH4Cl, NH4NO3, K2HPO4, KH2PO4, Na2HPO4, MgSO4*7H2O, FeSO4*7H2O and NaNO;
an organic started mix comprising yeast extract, malt extract, cane molasses and methyl-β-cyclodextrin;
a mix of branched-chain essential amino-acids and nitrogen fertilizers, wherein:
the branched-chain essential amino-acids comprise Na Leucine, Na Valine, Na Isoleucine and Na Glutamate at a ratio of 1:1:1:1, and
the nitrogen fertilizers comprise urea, uric acid and water soluble lecithin at a ratio of 2:1:1, wherein said liquid removes the dielectric contained in said decommissioned oil cable.

2. The liquid of claim 1, further comprising a defoamer.

3. The liquid of claim 1, further comprising a biocompatible antifoam mix comprising Na2EDTA, polydimethylsiloxane, simethicone and rapeseed oil.

4. The liquid of claim 1, wherein the organic started mix comprises:
40 g/L of the yeast extract;
40 g/L of the malt extract;
100 g/L of the cane molasses; and
1 g/L of the methyl-β-cyclodextrin.

5. The liquid of claim 1, wherein the mix of branched-chain essential amino-acids and nitrogen fertilizers comprises:
1-500 mg/L of the branched-chain essential amino-acids;
1-500 mg/L of the urea;
1-500 mg/L of the uric acid; and
1-500 mg/L of the water soluble lecithin.

6. The liquid of claim 3, wherein the biocompatible antifoam mix comprises:
500 mg/L of the Na2EDTA;
200 g/L of the polydimethylsiloxane;
50 g/L of the simethicone; and
100 mL/L of the rapeseed oil.

7. The liquid of claim 3, wherein bacterial growth culture medium comprises:
5-200 g/L of the organic started mix;
5-20 g/L of the mix of branched-chain essential amino-acids and nitrogen fertilizers; and
0.05-8 g/L of the bio-compatible antifoam mix.

* * * * *